United States Patent [19]

Smith

[11] 4,230,845

[45] Oct. 28, 1980

[54] POLYHYDROXY-ALKYL-3,5-DISUBSTITUTED-2,4,6-TRIIODOCARBANILATES

[75] Inventor: Kenneth R. Smith, Black Jack, Mo.

[73] Assignee: Mallinckrodt, Inc., St. Louis, Mo.

[21] Appl. No.: 938,342

[22] Filed: Aug. 31, 1978

Related U.S. Application Data

[62] Division of Ser. No. 512,004, Oct. 4, 1974, Pat. No. 4,125,709.

[51] Int. Cl.$^3$ .................... C07H 13/12; C07C 102/00; C07C 103/20

[52] U.S. Cl. .................... 536/4; 260/557 R; 260/558 D; 260/562 R; 536/26; 536/31; 424/5; 536/29; 536/53; 536/30

[58] Field of Search .................... 536/53, 4, 26, 29; 560/26, 29; 260/557 R, 558 D, 562 R

[56] References Cited

U.S. PATENT DOCUMENTS

| | | | |
|---|---|---|---|
| 2,969,386 | 1/1961 | McElroy | 560/26 |
| 3,721,700 | 3/1973 | Schuierer et al. | 560/26 |
| 4,065,293 | 12/1977 | Boroschewski et al. | 560/29 |
| 4,125,709 | 11/1978 | Smith | 536/53 |

*Primary Examiner*—Johnnie R. Brown
*Attorney, Agent, or Firm*—Senniger, Powers, Leavitt and Roedel

[57] ABSTRACT

Certain polyhydroxy-alkyl-3,5-disubstituted-2,4,6-triiodocarbanilates are useful as x-ray contrast agents. Representative of this class of compounds is the compound 1-[N-(2,4,6-triiodo-3-N,N-dimethylcarbamyl-5-N-methylcarbamyl)carbanilyl]-L-sorbose.

7 Claims, No Drawings

POLYHYDROXY-ALKYL-3,5-DISUBSTITUTED-2,4,6-TRIIODOCARBANILATES

CROSS-REFERENCE TO RELATED APPLICATION

This application is a division of my copending application Ser. No. 512,004, filed Oct. 4, 1974, now U.S. Pat. No. 4,125,709.

BACKGROUND OF THE INVENTION

This invention relates to the field of organic chemistry, and more particularly to novel polyhydroxyalkyl-3,5-disubstituted-2,4,6-triiodocarbanilates useful as non-ionic x-ray contrast media.

As is known, many 2,4,6-triiodobenzoic acid derivatives have been proposed and used as x-ray contrast agents. In general, it has been the practice to convert these compounds to salts, such as for example, the sodium and N-methylglucamine salts in order to render the compounds water-soluble and suitable for intravenous administration.

More recently, Almen et al. (U.S. Pat. No. 3,701,771, dated Oct. 31, 1972) have disclosed certain non-ionic N-(2,4,6-triiodobenzoyl)-sugar amine which are stated to be useful as x-ray contrast agents in the cerebrospinal cavities. In these compounds a polyhydroxyalkyl chain is coupled to an iodoaromatic moiety in order to impart water solubility without resorting to ionic species. Certain of the non-ionic compounds disclosed in this patent were reported to be highly soluble in water while others were reported to have a medium or low water solubility.

In certain instances, non-ionic x-ray contrast media have been found to be less toxic than their ionic counterparts. This is believed to be due at least in part to the fact that the non-ionic compounds, being substantially non-ionized in aqueous solution, create less of an osmotic imbalance than do ionic compounds, i.e., non-ionic x-ray contrast media contribute only one molecular species per iodinated moiety as compared to ionic x-ray contrast media which contribute two or more species per iodinated moiety.

An interest has developed, therefore, in the synthesis of water-soluble, non-ionic x-ray contrast media possessing low toxicity and high iodine content for use in the x-ray visualization of various areas of the body such as, for example, the cardiovascular system where high concentrations of contrast media are required in order to provide sufficient opacity.

SUMMARY OF THE INVENTION

Among the several objects of the invention may be mentioned the provision of novel polyhydroxyalkyl-3,5-disubstituted-2,4,6-triiodocarbanilates; the provision of such compounds which are useful for the preparation of non-ionic x-ray contrast media; the provision of certain novel intermediates which are useful in the preparation of such compounds; and the provision of methods of preparing such compounds. Other objects and features will be in part apparent and in part pointed out hereinafter.

The present invention is thus directed to compounds of the formula:

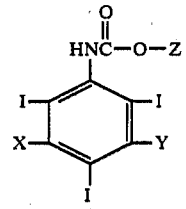

wherein X and Y are each non-ionizing the functions compatible with low toxicity and/or water solubility in the 2,4,6-triiodophenyl configuration and Z is the monovalent residue of a polyol, said monovalent residue containing not more than 7 carbon atoms in its chain or ring.

The invention is further directed to intermediate compounds of the formula:

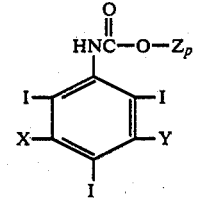

wherein X and Y are each non-ionizing functions compatible with low toxicity and/or water solubility in the 2,4,6-triiodophenyl configuration and $Z_p$ is selected from the group consisting of ester, acetal and ketal derivatives of a monovalent residue of a polyol, said derivatives containing at least one hydroxyl group in an unprotected form and said monovalent residue containing not more than 7 carbon atoms in its chain or ring.

The invention also includes the step in a method of preparing compounds of the formula:

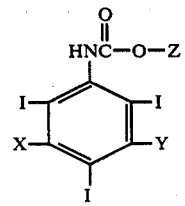

wherein X and Y are each non-ionizing functions compatible with low toxicity and/or water solubility in the 2,4,6-triiodophenyl configuration and Z is the monovalent residue of a polyol, said monovalent residue containing not more than 7 carbon atoms in its chain or ring, which comprises reacting a compound of the formula:

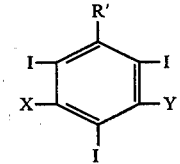

wherein X and Y are as defined above and R' is selected from the group consisting of isocyanate and carbamyl chloride functions, with a compound selected from the group consisting of the ester, acetal and ketal derivatives of a polyol, said derivatives containing at least one hydroxyl group in an unprotected form and said polyol containing not more than 7 carbon atoms in its chain or ring.

DESCRIPTION OF THE PREFERRED EMBODIMENTS

In accordance with the invention, it has been found that certain novel compounds of the following structure are useful as non-ionic x-ray contrast agents;

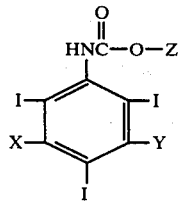

wherein X and Y are each non-ionizing functions compatible with low toxicity and/or water solubility in the 2,4,6-triiodophenyl configuration and Z is the monovalent residue of a polyol, said monovalent residue containing not more than 7 carbon atoms in its chain or ring.

Preferably, Z is the monovalent residue of a polyol from the group consisting of linear and branched chain polyols, cyclic polyols, acylamino polyols and alkyl glycosides.

The linear polyols may be those of the formula:

where $n = 1$ to 5 and include glycerol, sorbitol, manitol, xylitol and various other triols, tetrols, pentols, hexitols and hepitols. The linear polyols may also be aldoses of the formula:

where $n = 1$ to 5. Illustrative polyols of this type include aldotrioses such as D-glyceraldehyde, aldotetroses such as D-erythrose and D-threose, aldopentoses such as D-ribose, D-xylose and D-arabinose, aldohexoses such as D-glucose, D-mannose and D-allose and aldoheptoses such as D-allo-heptose. Further, the linear polyols may be ketoses of the formula:

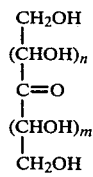

where $n + m = 0$ to 4. Among such polyols may be mentioned dihydroxyacetone, ketotetroses such as D-erythrulose, ketopentoses such as D-ribulose and D-xylulose, ketohexoses such as D-sorbose and D-fructose and ketoheptoses such as D-gluco-heptulose and D-gulo-heptulose. Additionally, the linear polyols may be deoxyaldoses such as 2-deoxyaldoses of the formula:

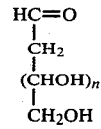

where $n = 1$ to 4 and the corresponding 3-deoxyaldoses, 4-deoxyaldoses, etc. Illustrative polyols of this type include 2-deoxy-D-ribose, 3-deoxy-xylose, 4-deoxy-D-glucose, 3-deoxy-D-mannose, etc.

Analogous branched chain polyols of the above types may also be utilized in the practice of the invention.

Various cyclic polyols may be employed as the source of the monovalent residue Z. These include polyhydroxy cycloalkanes such as hexahydroxy cyclohexanes (inositols), 2,4,6-trihydroxy cyclohexanes, pentahydroxy cyclopentanes and tetrahydroxy cyclobutanes, etc.

Acylamino polyols useful in the practice of the invention include N-acyl-deoxy-aldosamines of the formula:

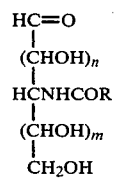

where $n + m = 1$ to 4 and R is lowwer alkyl and include compounds such as 2-acetylamino-2-deoxy-D-erythrose, 2-acetylamino-2-deoxy-D-ribose and 2-acetylamino-2-deoxy-D-glucose, and N-acyl-deoxy-ketosamines of the formula:

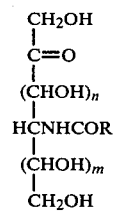

where $n + m = 1$ to 4 and R is lower alkyl (and other positional isomers) and include compounds such as 3-acetylamino-3-deoxy-D-ribulose, 3-acetylamino-3-deoxy-D-sorbose, 3-acetylamino-3-deoxy-D-fructose, etc.

Other useful acylamino polyols are deoxy-acylamino alditols of the formula:

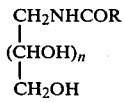

where $n = 1$ to 5 and R is lower alkyl. Among these polyols may be mentioned 1-deoxy-1-acetylamino-D-glucitol, 1-deoxy-1-acetylamino-D-sorbitol, 1-deoxy-1- acetylamino-D-mannitol and 1-deoxy-1-acetylamino-glycerol.

Additional acylamino polyols which may be used include various acylamino-cyclic polyols such as 1-acetylamino-2,3,4,5,6-pentahydroxy-cyclohexanes, 1-acetylamino-2,3,4,5-tetrahydroxy-cyclopentanes, etc.

The class of polyols useful in the invention further include alkyl glycosides of the formula:

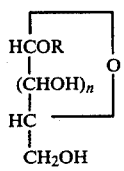

where $n=1$ to 4 and R is lower alkyl. Exemplary of such polyols are methyl $\alpha$-D-glucoside, methyl $\beta$-D-glucoside and methyl $\beta$-galactosides.

As indicated, the polyols of the acylamino type described above principally comprise lower acylamino polyol compounds. Also, as further indicated, the monovalent residue Z should contain not more than 7 carbon atoms and preferably 6 or 7 carbon atoms in its linear chain or ring.

The substituents in the 3- and 5-positions of the ring, namely X and Y, are non-ionizing functions compatible with low toxicity and/or water solubility in the 2,4,6-triiodophenyl configuraton. As is known by those skilled in the art, the term "detoxifying and/or solubilizing groups" has been used as a generic designation for a substantial number of functional groups whose occurrence in the meta-position in a 2,4,6-triiodinated moiety has come to be associated with compounds which exhibit a relatively low toxicity and/or a relatively high water solubility (cf. G. B. Hoey, P. E. Wiegert and R. D. Rands, Jr., "Organic Iodine Compounds as X-Ray Contrast Media:," in International *Encyclopedia of Pharmacology and Therapeutics*, Section 76, "Radio-Contrast Agents", P. K. Knoefel, Section Editor, Pergamon Press; Vol. 1, pp. 23–40, 54–73 (1971). While the use of such terminology originated in connection with 2,4,6-triiodobenzoic acid derivatives possessing relatively low toxicity and/or relatively high water solubility, the results set forth herein are consistent with the view that substantially the same non-ionizing functions are also compatible with low toxicity and/or water solubility in the triiodinated moiety of the non-ionic compounds of the present invention.

Among the non-ionizing functions which may constitute X and Y may be mentioned the following: lower alkoxy, e.g., methoxy and ethoxy; hydroxy-(lower alkoxy), e.g., 2-hydroxy-ethyoxy; lower alkoxy-(lower alkoxy) e,g., methoxy-ethoxy and ethoxy-propoxy; lower acylamino, e.g., acetamido and propionamido; lower acylamino-(lower alkyl), e.g., acetamido-methyl and acetamido-ethyl; lower acylamino-(lower acylamino), e.g., aceturamido; hydroxy-lower acylamino, e.g., hydroxyacetamido and hydroxy-propionamido; N-(lower alkyl)-lower acylamino, e.g., N-methylacetamido and N-methylpropionamido; lower alkylsulfonamido, e.g., methylsulfonamido and ethylsulfonamido; N-(lower alkyl)-lower alkylsulfonamido, e.g., N-methyl-ethylsulfonamido and N-ethyl-methylsulfonamido; 3,3-bis(loweralkyl)-ureido, e.g., 3,3-dimethylureido and 3-methyl-3-ethylureido; lower perfluoroacylamino, e.g., perfluoroacetamido and perfluoropropionamido; carbamyl; N-(lower alkyl) carbamyl, e.g., N-methylcarbamyl and N-ethylcarbamyl; N,N-di-(lower alkyl) carbamyl, e.g., N,N-dimethylcarbamyl and N,N-diethylcarbamyl; lower alkoxy-(lower acylamino), e.g., methoxy-acetamido and ethoxy-acetamido; lower alkoxy-alkoxy-(lower acylamino), e.g., methoxy-ethoxy-(acetamido) and methoxy-ethoxy-(acetamido); hydroxy and hydroxy-lower alkyl, e.g., hydroxymethyl and hydroxyethyl. As used herein, the term "acyl" means RCO where R is lower alkyl and the term "lower" (e.g., lower alkyl and lower alkoxy) means that the function contains between 1 and 6 carbon atoms. Those skilled in the art will recognize that functions of the above type other than those specifically enumerated may also constitute X and Y.

In another aspect of the invention, one of X and Y may be constituted by hydrogen or one of the functions enumerated above and the other of X and Y may be constituted by the function

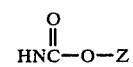

where Z is as previously defined.

In the method aspect of the invention, the novel end products represented by the first structure previously set forth are prepared by first reacting a precursor compound of the formula:

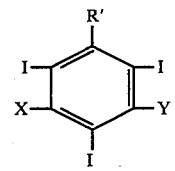

wherein X and Y ar each non-ionizing functions compatible with low toxicity and/or water solubility in the 2,4,6-triiodophenyl configuration and R' is an isocyanate or carbamyl chloride function, with an ester, acetal or ketal derivative of a polyol of the types previously described, the derivative containing at least one hydroxyl group in unprotected form. A mixture of precursor compounds where R' is isocyanate or carbamyl chloride may also be employed. Thus, the ester, acetal or ketal derivative represents a protected form of the polyol which contains at least one free hydroxyl group which reacts with the isocyanate or carbamyl chloride function of the precursor compound. Ordinarily, it is preferable that the derivative or protected polyol have not more than one primary and one secondary hydroxyl group in unprotected form. Where the derivative contains one primary and one secondary hydroxyl group in unprotected form, the reaction with the precursor compound occurs preferentially with the primary hydroxyl group.

Where it is desired to have X or Y in the end product be constituted by hydroxy, hydroxy-lower alkyl, hydroxy-(lower alkoxy) or hydroxy-lower acylamino functions which contain hydrogen atoms reactive with the isocyanate or carbamyl chloride function, they are present in the precursor compound of the formula set forth above in a protected form, i.e., as ester, acetal or ketal derivatives of such functions.

Exemplary ester protecting groups useful in the practice of the invention include formate, acetate, benzoate and cyclic carbonate while illustrative acetal and ketal protecting groups include benzylidene, methylene, cyclohexylidene, ethylidene, isopropylidene, tetrahydropyranoxy and similar groups. Other protecting groups known to those skilled in the art may also be employed.

In general, for example, the preferred protecting groups employed for protecting linear and branched polyols of the types previously described include the acetals of formaldehyde, acetaldehyde, benzaldehyde and other aldehydes and the ketals of acetone, cyclohexanone and other ketones. As will be recognized by those skilled in the art, the protecting group employed should be readily removable under relatively mild conditions so as to avoid any adverse effect on the carbamato function. By way of further example, protecting groups for glucose include ketals of acetone and cyclohexanone and acetals of benzaldehyde; protecting groups for xylose include ketals of acetone and cyclohexanone and esters derived from methyl chloroformate; protecting groups for arabinose include ketals of acetone and acetals of benzaldehyde; protecting groups for galactose include acetals of benzaldehyde and ketals of acetone; protecting groups for fructose include ketals of acetone and acetals of benzaldehyde; protecting groups for sorbose include ketals of acetone, 2-butanone and cyclohexanone; protecting groups for glucitol include ketals of acetone and acetals of acetaldehyde and benzaldehyde; protecting groups for mannitol include ketals of acetone and cyclohexanone and acetals of formaldehyde; protecting groups for dulcitol include ketals of acetone and acetals of formaldehyde and benzaldehyde; and protecting groups for xylitol include acetals of formaldehyde and benzaldehyde and ketals of acetone. The acetal protecting groups include internal and external acetals and mixed internal and external acetals. Either the D-compounds or the L-isomers or enantiomers may be used in the practice of the invention.

The reaction between the above-noted precursor compounds and the ester, acetal or ketal derivative of the polyol compound produces intermediates of the formula:

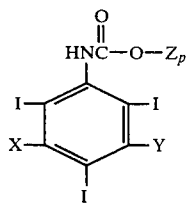

wherein X and Y are as previously defined and $Z_p$ is an ester, acetal or ketal derivative of a monovalent residue of a polyol, the derivative containing at least one hydroxyl group in an unprotected form. More specifically, X and Y may each be substituted by lower alkoxy, lower alkoxy-(lower alkoxy), lower acylamino, lower acylamino-(lower alkyl), lower acylamino-(lower acylamino), N-(lower alkyl)-lower acylamino, lower alkylsulfonamido, N-(lower alkyl)-lower alkylsulfonamido, 3,3-bis(lower alkyl)-ureido, lower perfluoroacylamino, carbamyl, N-(lower alkyl) carbamyl, N,N,-di-(lower alkyl) carbamyl, lower alkoxy-(lower acylamino) and lower alkoxy-alkoxy-(lower acylamino)functions and ester, acetal or ketal derivatives of hydroxy, hydroxy-lower alkyl, hydroxy-(lower alkoxy) and hydroxy-lower acylamino functions. Such intermediates are converted into the end products of the invention by removal of all of the protecting groups from the intermediate compounds through treatment with acid were $Z_p$ is an acetal or ketal derivative or with base where $Z_p$ is an ester derivative.

Alternatively, the novel products of the invention may be prepared by the following reaction scheme;

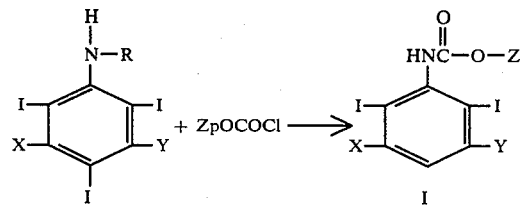

wherein X, Y and Z are as previously defined for the novel end products, R is hydrogen or lower alkyl and $Z_p$ represents a polyol function in protected form, i.e., in the form of the above-described ester, acetal or ketal derivatives of the polyol function with the derivatives containing at least one hydroxyl group in unprotected form. The reaction set forth first produces intermediate compounds in which the polyol moiety of the compounds of the invention is in protected form, these intermediates being converted into the end products of the formula shown by removal of the protecting groups as previously described.

The novel compounds of the invention may be used as x-ray contrast agents in various radiographic procedures including those involving cardiovascular visualization, myelography, ventriculography, coronary arteriography, intravenous pyelography, bronchography and urography. Certain compounds of the invention exhibit high water solubility and relatively low toxicity while others may exhibit the limited water solubility and relatively low toxicity required, for example, in oral radiographic procedures such as bronchography.

The following examples illustrate the invention.

EXAMPLE I
1-[N-(2,4,6-Triiodo-3-N,N-dimethylcarbamyl-5-N-methylcarbamyl)carbanilyl)]-L-sorbose 1. Preparation of 5-amino-2,4,6-triiodo-N-methylisophthalamyl chloride: II

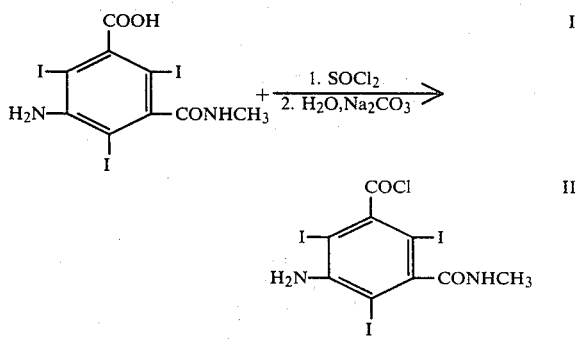

5-Amino-2,4,6-triiodo-N-methylisophthalamic acid (Hoey U.S. Pat. No. 3,145,197, dated Aug. 18, 1964; I; 572 g., 1 mole) was heated and stirred at reflux temperature in thionyl chloride (1.2 l.) for 4.5 hours. After concentration of the homogeneous reaction mixture under reduced pressure, the residue was dissolved in tetrahydrofuran (2.0 l.) and the cooled solution was extracted with a saturated aqueous solution of sodium carbonate and sodium chloride. The layers were separated and the organic layer was dried over sodium sulfate. The organic layer may be used directly to prepare 5-amino-2,4,6-triiodo-N,N,N'-trimethylisophthalamide (III) or it may be concentrated to provide the acid chloride which was pure by thin-layer chromatography (chloroform-ethyl) acetate-acetic acid, 30:30:1) and whose structure was confirmed by infrared analysis.

2. Preparation of 5-amino-2,4,6-triiodo-N,N,N'-trimethylisophthalamide; III

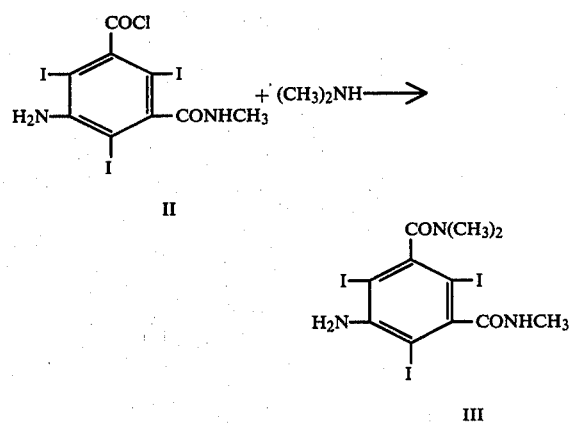

To chilled, 25% aqueous dimethylamine (1.3 l.) was added the solution of 5-amino-2,4,6-triiodo-N-methylisophthalamyl chloride (II; 1.0 mole) prepared as above in tetrahydrofuran while maintaining the solution at 20° C. After stirring overnight in an open beaker, the precipitated product (287 g. representing a yield of 48%) was collected by filtration and washed with methanol. A second group (111 g.; 18.5%) was obtained from the mother liquor. The product (m.p. 259°–263° C. with dec.) was pure by thin-layer chromatography (ethyl acetate-acetic acid 98.2) and its structure was confirmed by elemental infrared and proton magnetic resonance spectroscopic analyses.

Calc. for $C_{11}H_{12}I_3N_3O_2$: C, 22.06; H, 2.06; I, 63.56; N, 7.02; Found: C, 22.06; H, 2.17; I, 64.24; N, 6.90; C, 21.80; H, 2.06; I, 63.95; N, 6.94

3. Preparation of 2,4,6-triiodo-5-isocyanato-N,N,N'-trimethylisophthalamide; IV

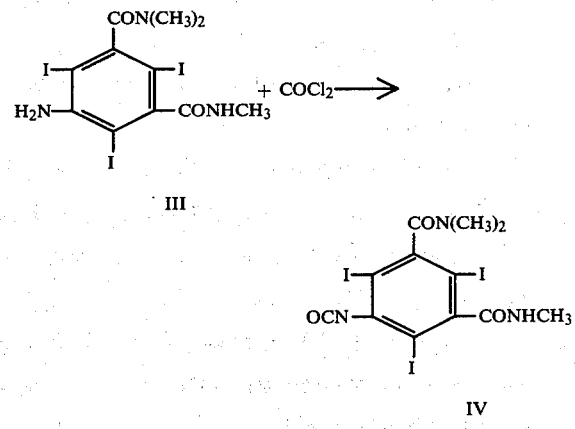

Dioxane (600 ml.) and 5-amino-2,4,6-triiodo-N,N,N'-trimethylisophthalamide (III; 119.8 g., 0.2 mole) were vigorously stirred at room temperature under a nitrogen atmosphere with phosgene (160 ml.) until dissolution was effected (ca. 48 hours). The excess phosgene and solvent were removed under reduced pressure to provide the slightly impure product as a white-glassy foam in nearly quantitative yield. The structure of the product was confirmed by infrared and proton magnetic resonance spectroscopic analyses. The purity of the product could not be ascertained by thin-layer chromatography (ethyl acetate-acetic acid, 98:2) owing to hydrolysis of the isocyanate on the plate.

4. Preparation of 2,3:4,6-di-O-isopropylidene-1-[N-(2,4,6-triiodo-3-N,N-dimethylcarbamyl-5-N-methylcarbamyl) carbanilyl]-L-sorbose; V

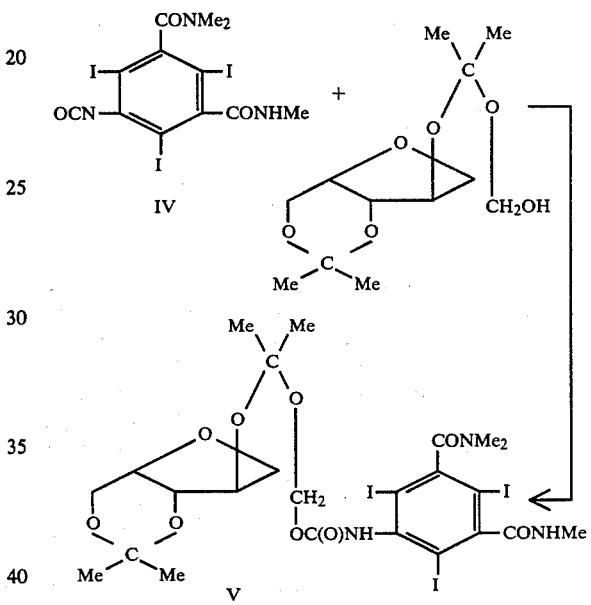

To a stirred solution of 2,4,6-triiodo-5-isocyanato-N,N,N'-trimethylisophthalamide (IV; 120.4 g., 0.17 mole) in dimethylformamide (500) was added a solution of 2,3:4,6-di-O-isopropylidene-L-sorbose (44.2 g., 0.17 mole) in dimethylformamide (250 ml.). After 3 hours, the reaction mixture was concentrated under reduced pressure (1.0 mm.); the residue was dissolved in dichloromethane, and was washed with 5% sodium bicarbonate solution, water and saturated brine. After drying the organic phase (Na$_2$SO$_4$), the solvent was removed under reduced pressure and the residue was triturated with ethyl acetate. After filtration to remove a white solid, the ethyl acetate was removed under reduced pressure to provide 114.8 g. of an off-white foam (representing a yield of 76%) which was sufficiently pure for the next step by thin-layer chromatography (ethyl acetate-acetic acid, 98:2). Recrystallization from ethyl acetate-cyclohexane provided an analytical sample (m.p. 196° C. (softens), 202°–210° C. (foams), 256° C. (dec.), whose infrared and proton magnetic resonance spectra confirmed the structure.

Calc. for $C_{24}H_{30}I_3N_3O_9$: C, 32.56; H, 3.42; I, 43.01; Found: C, 32.50; H, 3.61; I, 42.30

5. Preparation of 1-[N-(2,4,6-triiodo-3-N,N-dimethylcarbamyl-5-N-methylcarbamyl)carbanilyl]-L-sorbose; VI

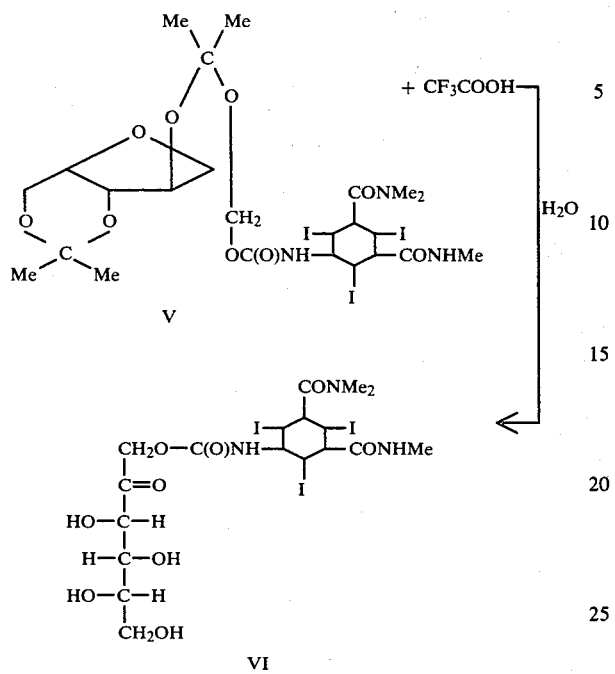

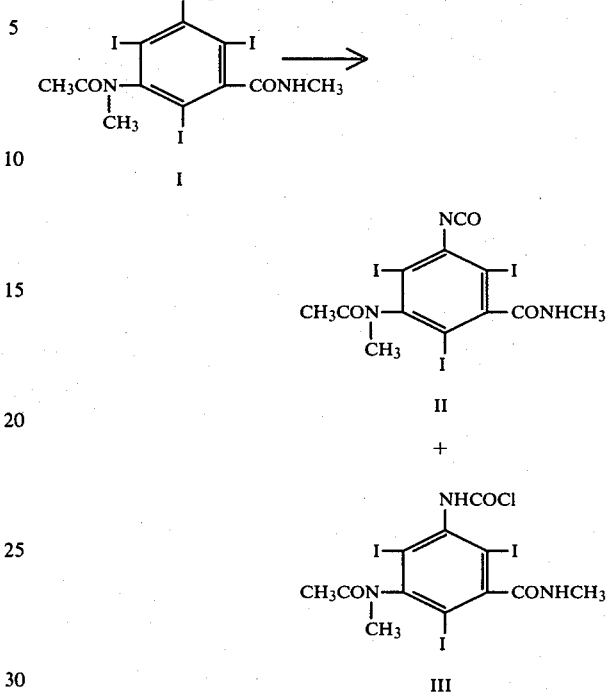

Trifluoroacetic acid (19 ml.) and water (1.9 l.) were added to a solution of 2,3:4,6-di-O-isopropylidene-1-[N-(2,4,6-triiodo-3-N,N-dimethylcarbamyl-5-N-methylcarbamyl) carbanilyl]-L-sorbose (V; 114.8 g.) in dioxane (1.15 l.) and the solution was heated at reflux for 5 hours and allowed to cool overnight. The solution was concentrated to a volume of 500 ml. and filtered to remove a white solid (which was discarded) and the filtrate was repeatedly extracted with 90% phenol, the aqueous layer being discarded. The combined phenolic extracts were washed with water, with the aqueous layer being discarded, and were diluted with ether. The phenolic-ethereal layer was repeatedly extracted with water, the organic layer being discarded, and the combined aqueous extracts were repeatedly extracted with chloroform-isopropyl alcohol (3:1) with the organic extracts being discarded. The aqueous layer was concentrated under reduced pressure (30 mm. to 0.05 mm.) to provide a white foam (45.8 g.; 165°–190° C. dec.) which was shown to be pure by thin-layer chromatography (chloroform-isopropyl alcohol. 6:4 and ethyl acetate-acetic acid-methanol, 78:2:20). The structure of the product was confirmed by infrared and proton magnetic resonance spectroscopic analyses and by elemental analysis. Initially, the water solubility of the compound was determined to be 100% (w/v); however, after standing for one month, the solubility decreased to 20% (w/v).

Calc. for $C_{18}H_{22}I_3N_3O_9$:C, 26.85; H, 2.75; I, 47.29; N, 5.22; Found: C, 26.75; H, 2.95; I, 46.90; N, 5.17

EXAMPLE II
6-[2,4,6-Triiodo-3-(N-methylacetamido)-5-(N-methylcarbamyl)carbanilyl]-D-galactose 1. Preparation of 2,4,6-triiodo-3-isocyanato-N-methyl-5-(N-methylacetamido)benzamide and 3-chlorocarbonylamino-2,4,6-triiodo-N-methyl-5-(N-methylacetamido)benzamide; II and III Dioxane (800 ml.) and 3-amino-2,4,6-triiodo-5-(N-methylacetamido)-benzamide (I; 119.8 g., 0.2 mole) were added to phosgene (212 ml.) and the reaction mixture stirred under a static nitrogen atmosphere for 48 hours. The excess phosgene and dioxane were removed under reduced pressure and the residue was dissolved in dichloromethane (450 ml.). Anhydrous ether was added to precipitate a dark-green solid and the precipitate was removed by filtration. The filtrate was concentrated in vacuo to provide the crude isocyanate and carbamyl chloride (II and III; 121 g., 91–97% crude yield) as shown by infrared analysis. This material is sufficiently pure for further reactions.

2. Preparation of 1,2:3,4-di-O-isopropylidene-α-D-galactopyranose.

The procedure employed was that of R. Stuart Tipson, "Methods in Carbohydrate Chemistry", Ed. R. L. Whistler and M. L. Wolfrom, Academic Press, New York, New York, 1963, Vol. II, p. 247.

3. Preparation of 1,2:3,4-di-O-isopropylidene-6-[2,4,6-triiodo-3-(N-methylacetamido)-5-(N-methylcarbamyl) carbanilyl]-D-galactose; IV

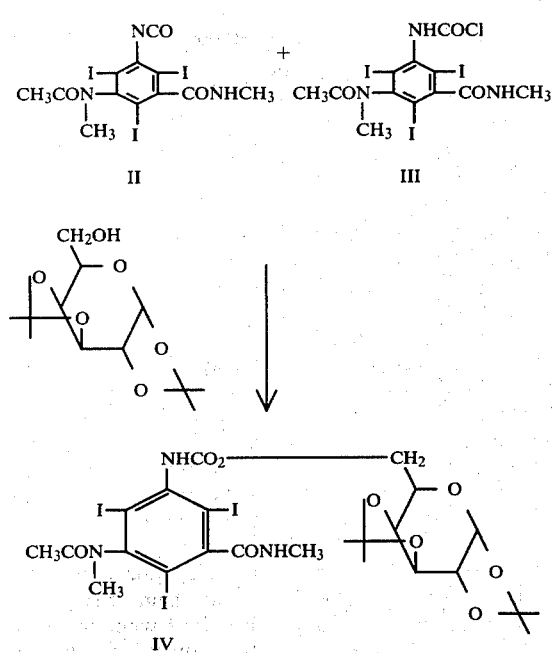

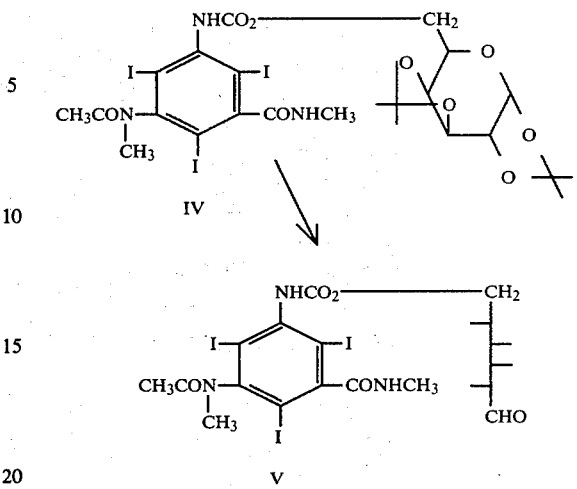

To a mixture of 1,2:3,4-di-O-isopropylidene-α-D-galactopyranose (4.42 g., 0.017 mole) and potassium carbonate (2.76 g., 0.02 mole) in dimethylformamide (75 ml.) was added a mixture of the isocyanate and carbamoyl chloride compounds (II and III; 12.04 g.; 0.017 mole; the number of moles is based on the amount of acetanilide (I) used to prepare the isocyanate-carbamoyl chloride mixture) dissolved in dichloromethane (36 ml.). After stirring overnight at room temperature, the reaction mixture was concentrated in vacuo. The residue was slurried in ethyl acetate (100 ml.); insolubles were removed by filtration. The filtrate was washed with 5% aqueous sodium bicarbonate solution, saturated brine solution, and evaporated. The residue was triturated in ether (150 ml.) overnight. The suspended solid was collected and dried at 70° C., 7.59 g. (50%). The identity of the product was confirmed by infrared analysis. Thin-layer chromatography (ethyl acetate-chloroform-acetic acid, 40:10:1) showed mainly one spot and indicated that no free sugar was present. The product was hydrolyzed to remove the protecting isopropylidene groups without further purification.

4. Preparation of 6-[2,4,6-triiodo-3-(N-methylacetmido)-5-(N-methylcarbamyl)carbanilyl]-D-galactose; V 1,2:3,4-Di-O-isopropylidene-6-[2,4,6-triiodo-3-(N-methylacetamido)-5-(N-methylcarbamyl)carbanilyl]-D-galactose (IV; 6.6 g., 0.0075 mole) was refluxed for 2 hours in a mixture of dioxane (69 ml.), water (115 ml.) and trifluoroacetic acid (1.15 ml. which was added last). The reaction mixture was concentrated to approximately two-thirds its original volume; insolubles were removed by filtration. The filtrate was adjusted to pH 7 with dilute sodium hydroxide and extracted with 90% phenol (4 × 25 ml.). The combined phenolic extracts were washed with water (4 × 25 ml.; an emulsion in the fourth wash was broken by the addition of a few drops of dilute hydrochloric acid), diluted with ether (300 ml.) and extracted with water (4 × 25 ml.). The combined water extracts were washed with a 3:1 chloroform-isopropyl alcohol mixture (2 × 100 ml.; contact time 30 min.), treated with decolorizing carbon ("Darco G-60"; 0.37 g.) for 1.5 days, and evaporated under reduced pressure to give 3.39 g. (56%) of product (V) as an off-white foam; m.p. 165°–195° C. (dec.); thin-layer chromatography (ethyl acetate-methanol-acetic acid, 80:20:2) showed two spots probably due to isomers. The infrared and nuclear magnetic resonance spectra were consistent with the assigned structure. The water solubility of the product was determined to be equal to or greater than 100% (w/v).

Calc. for $C_{18}H_{22}I_3N_3O_9$: C, 26.85; H, 2.75; I, 47.29; N, 5.22; Found: C, 26.89; H, 2.82; I, 47.32; N, 5.32

Toxicity evaluations in accordance with three different techniques were carried out on aqueous solutions of the compounds of Examples I and II. The techniques utilized are described below.

1. ACUTE INTRAVENOUS TOXICITY STUDIES IN MICE

Swiss Albino mice (Charles River) were dosed in the lateral tail vein with aqueous solutions of the above-noted iodinated compounds having an iodine concentration of 28.2% with a pH of 7.0–7.2. The solutions were injected at the rate of approximately 1 ml./min. Following injections, the animals were observed for immediate reactions and then daily throughout a seven day observation period. The $LD_{50}$ values were calculated by the method of Litchfield and Wilcoxon (J. of Pharmac. and Exptl. Therap. 96: 99–113, 1949).

2. INTRACEREBRAL TOXICITY IN MICE

Swiss Albino mice (Charles River) were used. Fixed volumes of aqueous solutions of the iodinated compounds were injected intracerebrally via a 27 gauge needle (¼ inch in length) according to the method of Haley et al. (Br. J. of Pharmac. 12:12–15, 1957). The animals were observed immediately following injections and daily throughout a seven day observation period. The $LD_{50}$ values were calculated by the method of Litchfield and Wilcoxon (J. of Pharmac. and Exptl. Therap. 96:99–113, 1949).

3. INTRACISTERNAL TOXICITY IN RATS

Sprangue-Dawley (Carworth) rats were used. The method used was a variation of the procedure outlined by Melartin et al. (Invest. Rad. 5: 13–21, 1970). After dosing, the animals were housed individually and observed for immediate reactions and periodically for a two day observation period. The $LD_{50}$ values were calculated according to the method of Litchfield and Wilcoxon (J. of Pharmac. and Exptl. Therap. 96:99–115, 1949).

The results of these toxicity elevations made on solutions of two compounds of the invention are set forth in Table 1.

TABLE 1

Toxicity Values of Two Compounds of the Invention

| Compound | $LD_{50}$ Value (mg. I/kg. body wt.) | | |
|---|---|---|---|
| | I.V.(Mice) | Intra-cerebral (Mice) | Intra-cisternal (Rats) |
| Example I | 3,027 | 1,450 | 13 |
| Example II | 2,300 | 222 | <20 |

The compounds of Examples I and II were employed in intravenous pyelographic studies carried out in dogs. At a dosage of 1000 mg. I/kg., very good contrast of the kidneys, collecting pelvises and urinary bladder was observed five minutes after injection into a dog of the compound of Example I. At a dosage of 155 mg. I/kg., the compound of Example II provided visualization of the kidneys one minute after injection into a dog and five minutes after injection, a better shadow of the kidneys was seen together with partial visualization of the ureters.

As will be apparent to those skilled in the art, other compounds within the scope of the invention in addition to those specifically disclosed in the above examples may be prepared by the same general methods.

In view of the above, it will be seen that the several objects of the invention are achieved and other advantageous results attained.

As various changes could be made in the above methods and products without departing from the scope of the invention, it is intended that all matter contained in the above description shall be interpreted as illustrative and not in a limiting sense.

What is claimed is:

1. A compound of the formula:

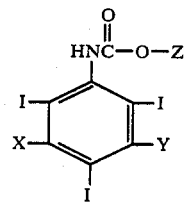

wherein X and Y are each selected from the group consisting of lower alkoxy, hydroxy-(lower alkoxy), lower alkoxy-(lower alkoxy), lower acylalkyl), lower acylamino-(lower acylamino), hydroxy-lower acylamino, N-(lower alkyl)-lower acylamino, lower alkylsulfonamido, N-(lower alkyl)-lower alkylsulfonamido, 3,3-bis-(lower alkyl)-ureido, lower perfluoroacylamino, carbamyl, N-(lower alkyl) carbamyl, N,N-di-(lower alkyl) carbamyl, lower alkoxy-(lower acylamino), lower alkoxy-alkoxy(lower acylamino), hydroxy and hydroxy-lower alkyl functions and Z is the monovalent residue of a polyol selected from the group consisting of cyclic polyols, acylamino polyols and alkyl glycosides, said monovalent residue containing not more than 7 carbon atoms in its chain or ring.

2. A compound as set forth in claim 1 wherein one of X and Y is selected from the group consisting of hydrogen and the functions set forth in claim 1 and the other of X and Y is

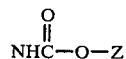

where Z is as defined in claim 1.

3. A compound as set forth in claim 1 wherein X and Y are each selected from the group consisting of lower acylamino, N-(lower alkyl)-lower acylamino, carbamyl, N-(lower alkyl) carbamyl and N,N-di-(lower alkyl) carbamyl.

4. A compound of the formula:

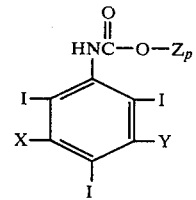

wherein X and Y are each selected from the group consisting of lower alkoxy, lower alkoxy-(lower alkoxy), lower acylamino, lower acylamino-(lower alkyl), lower acylamino-(lower acylamino), N-(lower alkyl)-lower acylamino, lower alkylsulfonamido, N-(lower alkyl)-lower alkylsulfonamido, 3,3-bis-(lower alkyl)-ureido, lower perfluoroacylamino, carbamyl, N-(lower alkyl) carbamyl, N,N-di-(lower alkyl) carbamyl, lower alkoxy-(lower acylamino), lower alkoxyalkoxy-(lower acylamino) functions and ester, acetal or ketal derivatives of hydroxy, hydroxy-lower alkyl, hydroxy-(lower alkoxy) and hydroxy-lower acylamino functions and $Z_p$ is selected from the group consisting of ester, acetal and ketal derivatives of a monovalent residue of a polyol selected from the group consisting of cyclic polyols, acylamino polyols and alkyl glycosides, said derivatives containing at least one hydroxyl group in an unprotected form and said monovalent residue containing not more than 7 carbon atoms in its chain or ring.

5. A compound as set forth in claim 4 wherein said derivatives contain not more than one primary and one secondary hydroxyl group in an unprotected form.

6. A compound as set forth in claim 4 wherein one of X and Y is selected from the group consisting of hydrogen and the functions set forth in claim 4 and the other of X and Y is

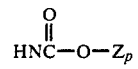

where $Z_p$ is as defined in claim 4.

7. A compound as set forth in claim 4 wherein X and Y are each selected from the group consisting of lower acylamino, N-(lower alkyl)-lower acylamino, carbamyl, N-(lower alkyl)carbamyl and N,N-di-(lower alkyl)carbamyl.

* * * * *

UNITED STATES PATENT AND TRADEMARK OFFICE
CERTIFICATE OF CORRECTION

PATENT NO. : 4,230,845

DATED : October 28, 1980

INVENTOR(S) : Kenneth R. Smith

It is certified that error appears in the above—identified patent and that said Letters Patent is hereby corrected as shown below:

Column 3, line 11, "agents;" should read -- agents: --. Column 4, line 36, "lowwer" should read -- lower --. Column 5, line 66, "(loweralkyl)" should read -- (lower alkyl) --. Column 6, line 39, "ar" should read -- are --. Column 7, line 58, "substituted" should read -- constituted --. Column 10, line 44, "(500)" should read -- (500 ml.) --. Column 16, line 13, "acylalkyl" should read--acylamino, lower acylamino-(lower alkyl --. Column 16, line 60, "alkoxyalkoxy" should read -- alkoxy-alkoxy--

Signed and Sealed this

Seventeenth Day of March 1981

[SEAL]

Attest:

RENE D. TEGTMEYER

Attesting Officer     Acting Commissioner of Patents and Trademarks